US00PP21323P2

(12) United States Plant Patent
Smith

(10) Patent No.: US PP21,323 P2
(45) Date of Patent: Sep. 28, 2010

(54) ***CHRYSANTHEMUM* PLANT NAMED 'NUTTY YOFIONA'**

(50) Latin Name: *Chrysanthemum×milfolium*
Varietal Denomination: Nutty Yofiona

(75) Inventor: Mark A. Smith, Fort Myers, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/459,627

(22) Filed: Jul. 6, 2009

(51) Int. Cl.
*A01H 5/00* (2006.01)

(52) U.S. Cl. ..... Plt./290

(58) Field of Classification Search ..... Plt./290
See application file for complete search history.

*Primary Examiner*—June Hwu
(74) *Attorney, Agent, or Firm*—S. Matthew Edwards

(57) ABSTRACT

A new *Chrysanthemum* plant named 'Nutty Yofiona,' particularly distinguished by the medium size, red-orange decorative-type flowers, medium green foliage, freely branching with small to medium size, rounded and mounded plant habit.

1 Drawing Sheet

Latin name of the genus and species of the plant claimed: *Chrysanthemum×morifolium.*

Varietal denomination: 'Nutty Yofiona'.

BACKGROUND OF THE NEW PLANT

The present invention comprises a new *Chrysanthemum*, botanically known as *Chrysanthemum×morifolium*, and hereinafter referred to by the variety name 'Nutty Yofiona'.

The new cultivar 'Nutty Yofiona' has medium size, red-orange decorative-type flowers, medium green foliage, freely branching with small to medium size, rounded and mounded plant habit.

'Nutty Yofiona' originates as a natural whole plant mutation of 'Yofiona,' U.S. Plant Pat. No. 16,963. 'Nutty Yofiona' was discovered and selected by the inventor as a single flowering plant within a population of the parent cultivar in a field trial in Alva, Fla., in December 2005. The parent cultivar 'Yofiona' has more coral-bronze colored flowers, darker green foliage, fewer and more yellow-green phyllaries, natural season flowering response that is 2 days faster.

The first act of asexual reproduction of 'Nutty Yofiona' was accomplished when vegetative cuttings were propagated from the initial selection in February 2006 in a controlled environment in Alva, Fla.

BRIEF SUMMARY OF INVENTION

Horticultural examination of plants grown from cuttings of the plant initiated in February 2006, and continuing thereafter, has demonstrated that the combination of characteristics as herein disclosed for 'Nutty Yofiona' are firmly fixed and are retained through successive generations of asexual reproduction.

'Nutty Yofiona' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Chrysanthemum* as a new and distinct variety.

Plant Breeder's Rights for this cultivar have not been applied for. 'Nutty Yofiona' has not been made publicly available more than one year prior to the filing of this application.

BRIEF DESCRIPTION OF THE PHOTOGRAPHS

The accompanying photographic drawing shows typical flower and foliage characteristics of 'Nutty Yofiona' with colors being as true as possible with an illustration of this type. The photographic drawing shows a flowering potted plant of the new variety, and a close-up of the flowers.

DETAILED BOTANICAL DESCRIPTION

The plant descriptions, measurements and aforementioned photographs were taken in Salinas, Calif. in June 2009 under natural light. These plants were started and grown in six inch pots in Alva, Fla. and were shipped to California in late May 2009. Plants were grown under conditions which approximate those generally used in commercial potted *Chrysanthemum* production. These plants used in the photograph and descriptions were about 10 weeks old.

Color references are made to The Royal Horticultural Society Colour Chart (R.H.S.) 2001.

TABLE 1

DIFFERENCES BETWEEN THE NEW VARIETY 'NUTTY YOFIONA' AND A SIMILAR VARIETY

| | 'Nutty Yofiona' | 'Flashy Yogretchen' (U.S. Plant Pat. No. 17,846) |
|---|---|---|
| Flower size: | Larger | Smaller |
| Petiole length: | Longer | Shorter |
| Ray floret length: | Little shorter | Little longer |
| Flower color retention: | Better | Not as good |
| Plant habit: | Shorter, less spread | Little taller, more spread |
| Natural season flowering response: | 5-7 days faster | 5-7 days slower |

Plant:
*Form, growth and habit.*—Herbaceous decorative garden-type; stems upright and outwardly spreading, freely branching, strong and moderately vigorous growth habit.
*Plant height.*—19-22 cm.
*Plant height (inflorescence included).*—24-28 cm.
*Plant width.*—38-44 cm.
*Garden performance and tolerance to weather.*—Good.
*Crop time to flowering.*—About 44-49 days.

Roots:
*Number of days to initiate roots.*—4 days at about 21 degrees C.
*Number of days to produce a rooted cutting.*—4 days at 21 degrees C.
*Type.*—Fine, fibrous, free branching.
*Color.*—RHS N155B but whiter.

Foliage:
*Arrangement.*—Alternate, simple.
*Immature, leaf color, upper surface*—Closest to RHS 137A.
*Lower surface.*—Closest to RHS 138B.
*Mature, leaf color, upper surface.*—Closest to RHS 137A.
*Lower surface.*—Closest to RHS 138B.
*Length.*—5.8-6.6 cm.
*Width.*—3.5-4.8 cm.
*Shape.*—Ovate.
*Base shape.*—Attenuate.
*Apex shape.*—Mucronulate.
*Margin.*—Palmately lobed; slightly incised and serrate.
*Texture, upper surface.*—Bifid T-shaped hairs.
*Lower surface.*—Bifid T-shaped hairs.
*Color of veins, upper surface.*—RHS 146D.
*Color of veins, lower surface.*—RHS 146D.
*Petiole color.*—RHS 146D.
*Length.*—1.0-1.5 cm.
*Diameter.*—0.4 cm.
*Texture.*—Bifid T-shaped hairs.

Stem:
*Quantity of main branches per plant.*—8-10.
*Quantity of leaves per branch.*—12-14.
*Color of stem.*—Closest to RHS 147B.
*Length of stem.*—17-21 cm.
*Diameter.*—0.4 cm.
*Length of internodes.*—0.5-1.3 cm.
*Texture.*—Bifid T-shape hairs.
*Color of peduncle.*—Closest to RHS 147B, but appears lighter with heavy amount of hairs.
*Length of peduncle.*—5.5-7.5 cm.
*Peduncle diameter.*—0.15-0.2 cm.
*Texture.*—Bifid T-shaped hairs.

Inflorescence:
*Type.*—Compositate type, solitary inflorescences (decorative-type) borne terminally above foliage, ray florets arranged acropetally on a capitulum.
*Blooming habit.*—Natural season flowering around mid-September
*Quantity of inflorescences per plant.*—About 130-145.
*Quantity of inflorescences per lateral stem.*—About 14-20.
*Lastingness of individual blooms on the plant.*—4 weeks.
*Fragrance.*—Slightly spicy.

Bud (just before opening/showing color):
*Color.*—RHS 59A.
*Length.*—0.6-0.8 cm.
*Width.*—0.6-0.7 cm.
*Shape.*—Oblate.

Immature inflorescence:
*Diameter.*—3.0-3.5 cm.
*Color of ray florets, upper surface.*—Closest to RHS N34A.
*Lower surface.*—Between RHS 180B and RHS 180C with RHS 163C basally.

Mature inflorescence:
*Diameter.*—4.0-4.6 cm.
*Depth.*—1.5-2.0 cm.
*Total diameter of 'disc'.*—0.2-0.4 cm.
*Receptacle height.*—0.5 cm.
*Receptacle diameter.*—0.6-0.7 cm.

Ray florets:
*Average quantity of florets.*—About 165 in numerous whorls.
*Color of florets, upper surface.*—Closest to RHS 179A fading to between. RHS 172A to RHS 172B; with a hint of RHS 1B basally.
*Lower surface.*—RHS 172C, with RHS 163C margins and RHS 3B basally.
*Length.*—1.2-1.4 cm.
*Width.*—0.4-0.5 cm.
*Shape.*—Elliptical.
*Apex shape.*—Praemorse.
*Margin.*—Entire.
*Texture, upper surface.*—Papillose.
*Lower surface.*—Papillose.

Disc flowers:
*Average quantity of florets.*—About 20-30.
*Color of florets.*—RHS 13A towards apex and RHS 1C basally.
*Length.*—0.3-0.4 cm.
*Width.*—0.1 cm.
*Shape.*—Tubular, enlongated.
*Apex shape.*—Acute, 5 pointed.

Phyllaries:
*Quantity.*—About 25.
*Color, upper surface.*—Larger ones are RHS 137A, smaller ones are RHS 137B.
*Lower surface.*—Larger ones are RHS 137A, smaller ones are RHS 137B.
*Length.*—0.5-0.7 cm.
*Width.*—0.2-0.3 cm.
*Shape.*—Ligulate.
*Apex shape.*—Acute.
*Based.*—Fused.
*Margins.*—Entire; papery and translucent.
*Texture, upper surface.*—Bifid T-shaped hairs.
*Lower surface.*—Bifid T-shaped hairs.

Reproductive organs:
*Gynoecium.*—Found on both floret types.
*Pistil quantity.*—1.
*Length.*—0.5-0.6 cm.
*Style color.*—RHS 1B.
*Style length.*—0.4-0.5 cm.
*Stigma color.*—RHS 6A.
*Stigma shape.*—Biparted.
*Ovary color.*—RHS 155C.
*Androecium.*—Found on only disc florets.
*Stamen quantity.*—4-5.

*Color of filaments.*—RHS 1C.
*Length filaments.*—0.2-0.25 cm.
*Anther color.*—RHS 6A.
*Anther length.*—0.15 cm.
*Anther shape.*—Oblong to ligulate.
*Color of pollen.*—RHC 13C.
*Pollen amount.*—Moderate.
*Fertility/seed set.*—Has not been observed on this hybrid.

Disease/pest resistance: Disease resistance or susceptibility has not been observed on this hybrid.

What is claimed is:

1. A new and distinct variety of *Chrysanthemum* plant named 'Nutty Yofiona,' substantially as illustrated and described herein.

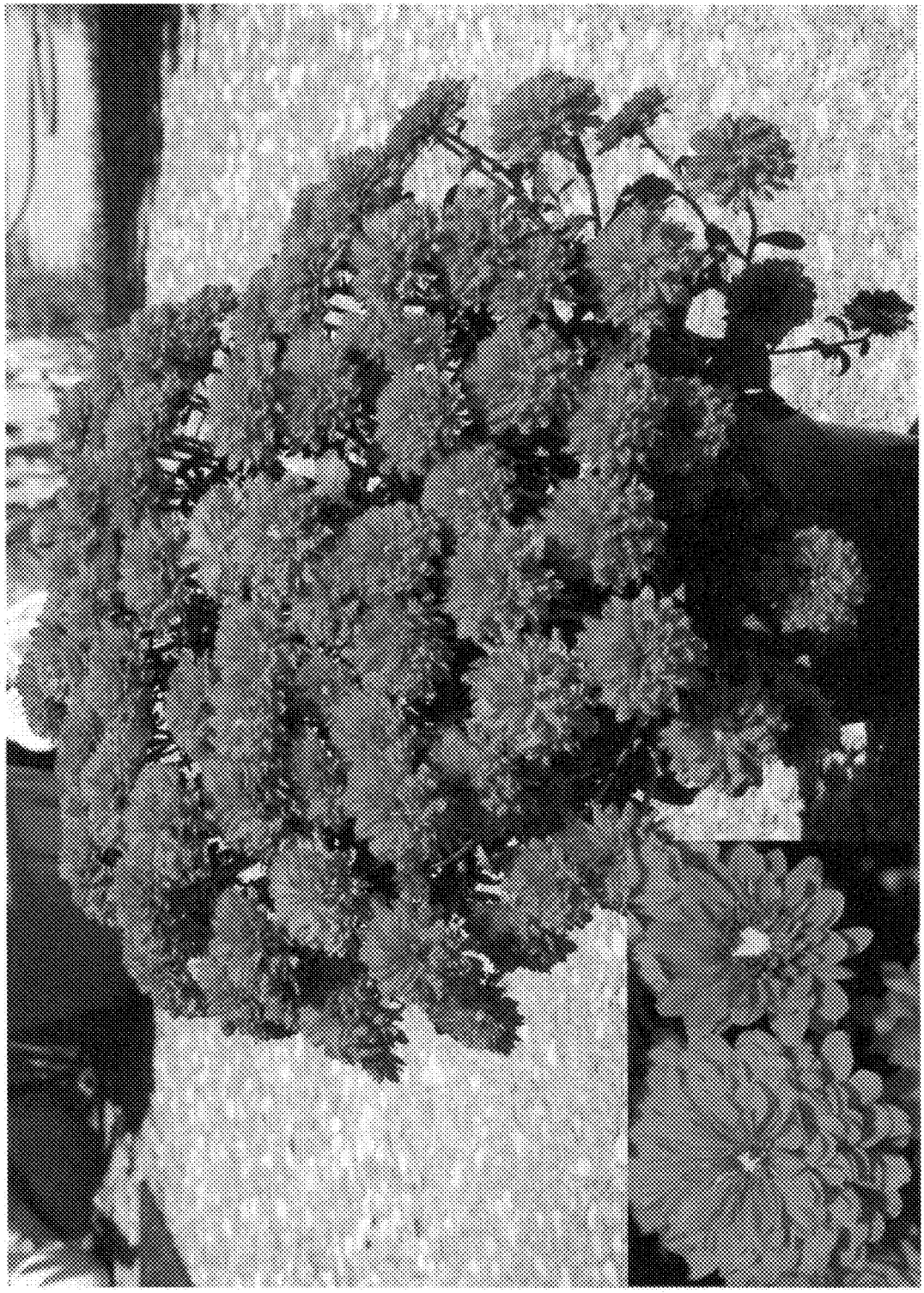

* * * * *